United States Patent [19]

Jäerisch et al.

[11] 4,167,337
[45] Sep. 11, 1979

[54] INTERFEROMETRIC APPARATUS AND PROCESS

[75] Inventors: Walter Jäerisch, Boeblingen; Günter Makosch, Sindelfingen-Maichingen; Arno Schmackpfeffer, Boeblingen, all of Fed. Rep. of Germany

[73] Assignee: International Business Machines Corporation, Armonk, N.Y.

[21] Appl. No.: 806,132

[22] Filed: Jun. 13, 1977

[30] Foreign Application Priority Data

Jun. 19, 1976 [DE] Fed. Rep. of Germany ....... 2627609

[51] Int. Cl.$^2$ ............................................. G01B 9/02
[52] U.S. Cl. .................................... 356/354; 356/239; 356/360
[58] Field of Search ................... 356/106 R, 109, 111, 356/237, 238, 234

[56] References Cited

U.S. PATENT DOCUMENTS 3,633,037  1/1972  Laugenbeck .................... 356/111 X

FOREIGN PATENT DOCUMENTS 2150110  4/1972  Fed. Rep. of Germany .
469882   8/1975  U.S.S.R. .................................... 356/109

Primary Examiner—John K. Corbin
Assistant Examiner—Matthew W. Koren
Attorney, Agent, or Firm—Theodore E. Galanthay

[57] ABSTRACT

Disclosed is an interferometric apparatus and method for the inspection and detection of overlay errors characterized in that two plane polarized laser beams are directed onto the surface to be inspected, the angle included by these two beams being dimensioned in such a way that the radiation generating the plus or minus first order of the diffraction pattern of one beam is parallel to the other beam, thus generating an interference field which in the absence of overlay errors consists of an homogeneous fringe pattern while in the presence of such errors the fringe pattern is locally distorted. In a first embodiment, a first component of a laser beam is deflected onto a viewing screen by a beam splitter while a second component passes through the beam splitter to a mirror. The position and angle of the mirror is determined by the first order diffraction characteristics of the grating (object). The second component provides a first order of diffraction which interferes with the first component, producing an interference pattern on the viewing screen.

8 Claims, 6 Drawing Figures

INTERFEROMETRIC APPARATUS AND PROCESS

BACKGROUND OF THE INVENTION

1. Field of the Invention

This invention relates to an interferometric apparatus and process for determining and measuring defects, by means of the interference of beams modulated and not modulated at the object. The invention further relates to an improved interferometric apparatus and process for the positioning of objects showing periodically structurized surfaces.

2. Description of the Prior Art

In many technical fields, for instance in the production and testing of the imaging quality of high resolution optical systems, or in the fabrication and examination of gratings and grating-like structures it is necessary to detect and measure the presence and magnitude of irregularities or disturbances of the periodicity of objects with periodically structurized surfaces. The transmission properties of high resolution imaging systems used in the manufacture of integrated circuits must be checked for each setting. The best way to do this is to check and measure a micro-grating that is made with the system to be examined.

In the fabrication of semiconductor integrated circuits, a semiconductor wafer having a surface area of approximately 5 cm$^2$ generally has thousands of circuits thereon. Frequently, as in the case of bistable storage circuits, many of these circuits are identical to each other. Also, the masks used for making the integrated circuits consist of periodical structures with grating constants of 1 to 5 $\mu$m. Deviations from the periodicity in general cause disturbances of the electric properties of the integrated circuits made thereby. The same applies also to the integrated circuits themselves.

Disturbances of the periodicity of the transmitted patterns can also occur when using so-called "step-and-repeat" cameras where it is well known that the light pattern transmitted onto a photoresist-coated semiconductor wafer is produced by transmitting hundreds or even thousands of precisely aligned partial patterns by means of a corresponding number of individual exposures.

The importance of maintaining an optimum periodicity and a maximum positional precision of the transmitted patterns is evident, inter alia, from the fact that in the production of integrated circuits, during 20 to 30 successive production steps, 20 to 30 precisely aligned and partly overlapping light patterns are applied. The line widths and spacings of said light patterns are in the order of a few $\mu$m.

In view of the trend towards integrated circuits with decreasing dimensions of the structural details and increasing packing densities, requirements for exact dimensional stability and periodicity of the transmitted patterns, as well as measurements permitting a checking of these characteristics are increasingly important.

In the known prior art, these measurements could be performed only by means of comparative measurings, for instance between two masks or between a mask and a semiconductor wafer. Since this kind of measuring involved specific test masks and a multitude of measurement data, as well as their correlation with the respective measurement data of the reference objects these processes, apart from the high amount of apparatus and costs they involved, could not be applied for the continuous checking of the production.

German Offenlegungsschrift No. 2,150,110 describes a process for determining the displacement or deformation of a periodically structurized object, where two beams derived from a common beam are applied onto the object in such a manner that two different diffraction orders differing from the zero'th order, of the two wavefronts are combined and brought into interference by an imaging element. Since according to this process both beams are influenced by the structure to be examined there is, apart from a strongly reduced sensitivity, also the disadvantage that disturbances appearing in the interference field cannot be correlated with specific locations of the objects which are being examined. This process involves not only an increased amount of apparatus but also additional inaccuracies which are due to the imaging errors of the imaging systems used.

SUMMARY OF THE INVENTION

It is an object of the present invention to provide an improved apparatus and method for determining and measuring errors or deviations from the periodicity or the rotational position of objects having grating-like structures.

It is another object of this invention to carry out such measurements, in a simple manner and with a relatively small amount of apparatus, in one operational step in fractions of seconds, visually or automatically.

Lastly, it is an object of this invention to align objects with grating-like structurized surfaces in a simple manner.

One step visual overlay inspection of the entire surface of a mask or a semiconductor wafer or chip is achieved by directing two laser beams onto the surface to be inspected. The angle included by these two beams is chosen in such a way that one of the beams is parallel to the radiation which generates the plus or minus first order of the diffraction pattern generated by the other beam. In the absence of overlay defects, the interference field formed by the minus or plus first diffraction order of one beam with the other beam takes the form of a homogeneous pattern of interference fringes. In the presence of overlay errors, this pattern displays irregularities or distortions indicating the location, nature and magnitude of said errors. By appropriate scanning this method can be made fully automatic.

Apart from its simplicity and the very small amount of apparatus involved, the process as disclosed by the invention presents in particular the considerable advantage that contrary to all other known interferometric processes it is independent of the surface smoothness of the surface to be examined since only structural deviations in the object plane (xy plane) take effect as distortions of the interference fringe system generated, whereas deviations orthogonal to that surface (z direction) are without any influence on the interference pattern. In this manner, the disadvantages of the Stoke interferometer where not only object changes in the xy plane, but also grating unevenness (z direction) influence the measuring results, are practically completely avoided.

The foregoing and other objects, features, and advantages of this invention will be apparent from the following and more particular description of preferred embodiments, as illustrated in the accompanying drawings.

IN THE DRAWINGS

DESCRIPTION OF THE PREFERRED EMBODIMENTS

Figure 1:
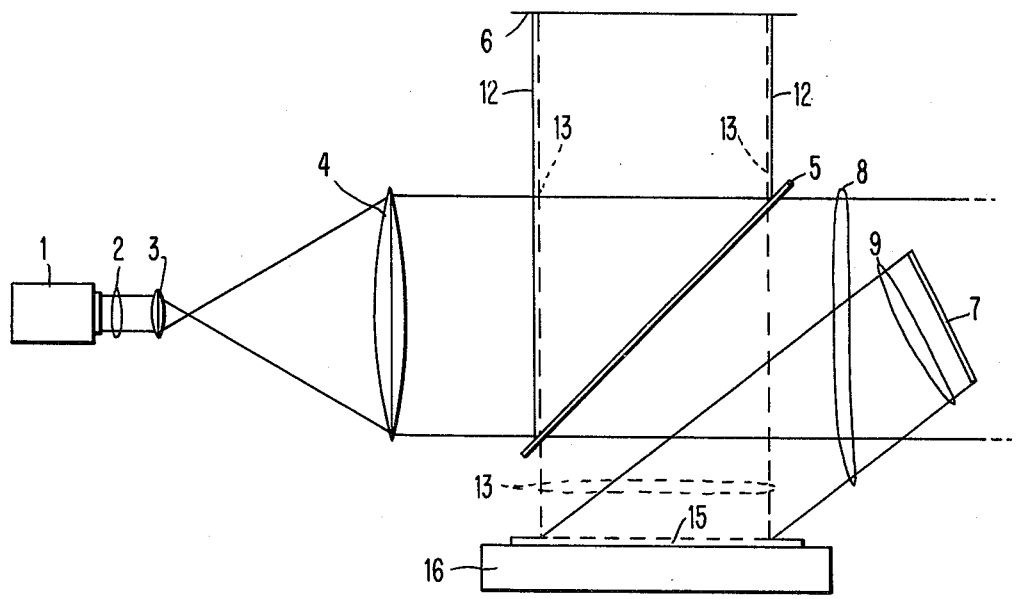
FIGS. 1 and 2 are schematic diagrams of embodiments of the invention where the first order diffracted at a reflection or transmission grating is superimposed on a beam deflected by a beam splitter.

Refer now to FIG. 1 which shows how the monochromatic and coherent beam 2 generated by a light source 1 designed for instance as a laser, is expanded by lenses 3 and 4 and directed to a beam splitter 5. A first component of the beam 12 is reflected upward by beam splitter 5 as shown by solid lines, and impinges on an observation screen 6 without being affected by object 15. A portion of a second component 8 passing through beam splitter 5 is reflected by a mirror 7 as beam 9 onto the object 15. The first diffraction order 13 represented by dashed lines, passes through beam splitter 5 and, together with the first component 12 which is not affected by object 15, impinges on a display means such as observation screen 6. The arrangement is such that with a given grating constant of the grating-like structurized object 15 to be tested the two components 12 and 13 extend in parallel to each other and in the range of observation screen 6 generate a homogeneous intensity distribution or, with a low divergence, an interference fringe field with uniform spacings. When angularly rotating the grating (object 15) with respect to the plane of incidence, an interference fringe field with equal spacings is obtained, provided the grating is perfect. In case of irregularities of the grating structure of the object 15 to be tested, the direction of the first order diffracted in the zones showing these defects changes, so that there will be a disturbance of the uniformity of the field of interference fringes visible in the range of observation screen 6. If the actual grating constant differs from the nominal grating constant the direction of the first diffraction order changes accordingly, so that there will be a change of the field of interference fringes visible in the range of observation screen 6. A change of the angular position around an axis that is parallel to the drawing plane is equivalent to a change of the grating constant of the grating structure of object 15 to be tested, and subsequently also influences the field of interference fringes visible in the range of observation screen 6. Thus, objects having the properties of a reflection grating are readily analyzed for deviations from periodic regularity.

Figure 2:
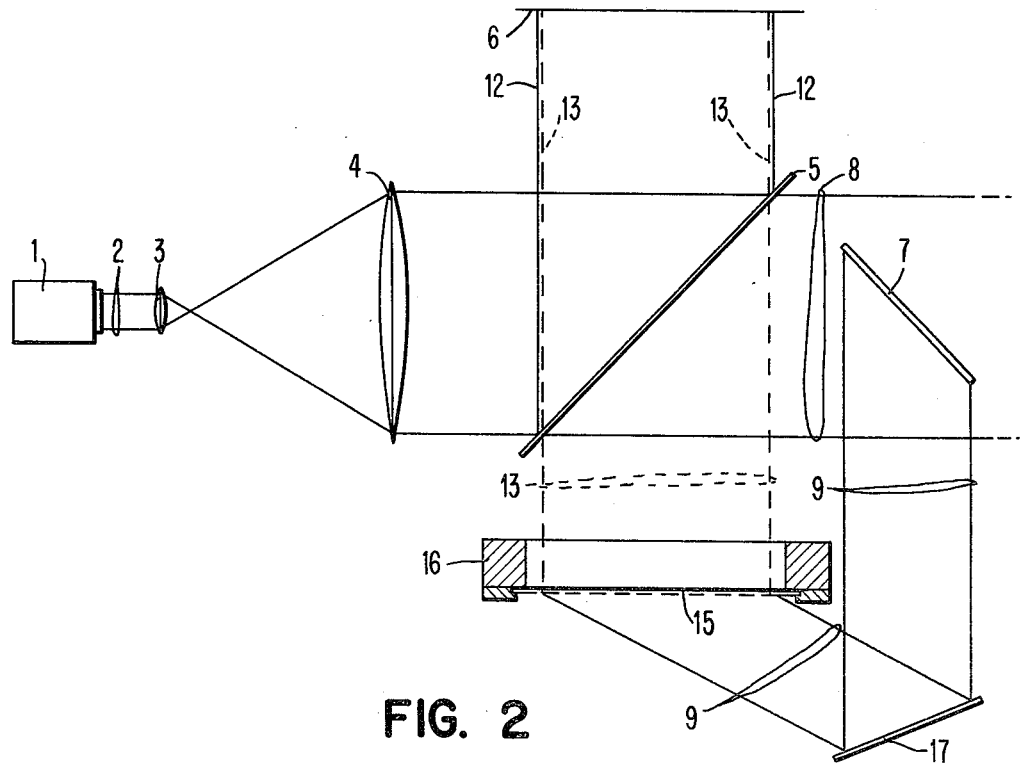

Refer now to FIG. 2 in which corresponding elements have been labelled with corresponding reference numerals. The apparatus of FIG. 2 is capable of testing an object having the properties of a transmission grating. A coherent and monochromatic beam 2 emanating from a light source 1 which is designed for instance as a laser, is expanded by lenses 3 and 4 and directed to a beam splitter 5. A component 12 reflected at this beam splitter and represented by solid lines reaches an observation screen 6 without being influenced by the object 15 to be measured. A portion of component 8 passing through beam splitter 5 is reflected by mirrors 7 and 17 as component 9, at an angle differing from 0°, to an object 15 having the characteristics of a transmission grating. The first diffraction order 13 of this radiation passes beam splitter 5 from below and reaches observation screen 6 as component 13, and is affected by object 15, together with component 12, which is not affected by the object 15. An interference fringe field as shown for instance in FIG. 5 (undisturbed) or FIG. 6 (disturbed) appears at the observation screen 6.

The arrangement is such that with a uniform structure and with a predetermined grating constant of object 15, the two components 13 and 12 are parallel to each other so that, in the range of observation screen 16, they generate a predetermined interference fringe field with uniform pattern spacing.

Figure 5:
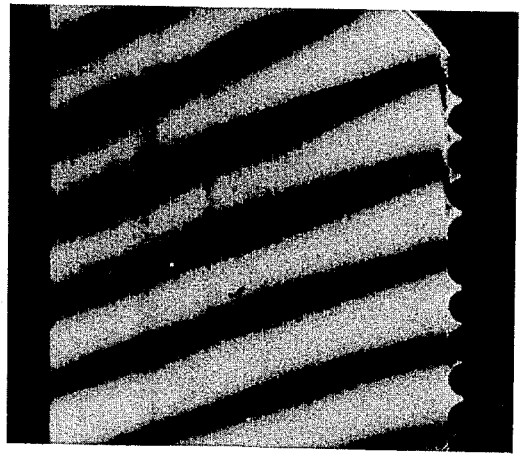
FIGS. 5 and 6 are photographs of interference fringe fields for constant undisturbed and locally disturbed gratings, respectively.
Figure 6:
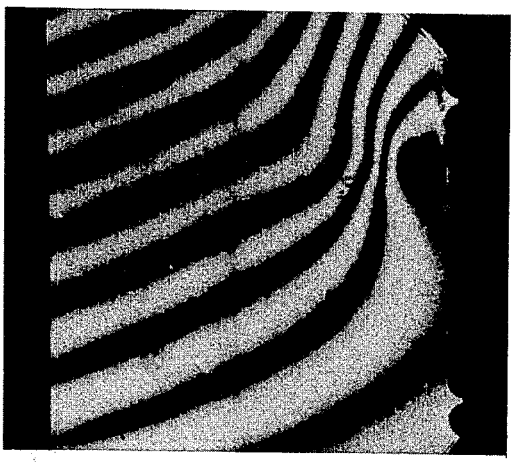

The statements made in connection with the description of FIG. 1 regarding the generation of the pattern shown in FIG. 5 also apply to the embodiment of FIG. 2. If in specific areas of object 15, there appear disturbances of the uniform grating structure, the direction of the first order diffracted in these areas is altered which leads to corresponding disturbances of the interference fringe field visible on the observation screen 6. Such an interference fringe field is shown in FIG. 6. A deviation of the grating constant or of the angle position of object 15 to be measured also leads to changes of the direction of the first order of diffraction, and thus to changes of the interference field which becomes visible at observation screen 6.

Figure 3:
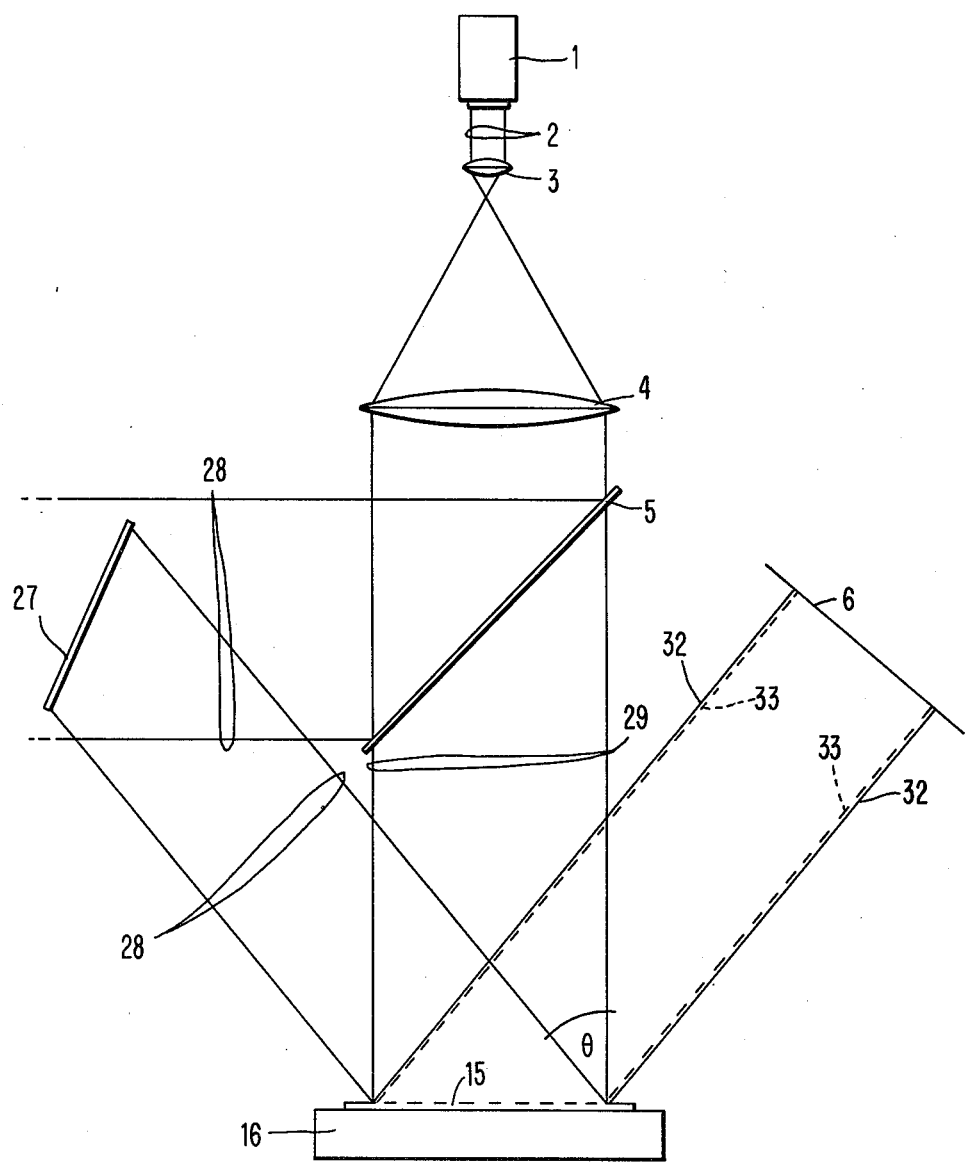
FIGS. 3 and 4 are schematic diagrams of alternate embodiments of the invention where the zero'th and the first order of two beams diffracted at a reflection or transmission grating are superimposed.

Refer now to FIG. 3 which illustrates an embodiment for checking an object 15 to be measured which shows the characteristics of a reflection grating. Corresponding reference numerals to previous drawings are again utilized. A monochromatic and coherent light beam 2 emanating from a light source 1 that is for instance designed as a laser is expanded by lenses 3 and 4 and directed to a beam splitter 5. A component 28 reflected at this beam splitter is reflected at a mirror 27 and impinges on object 15 to be measured. The zero'th order 32 of this radiation diffracted at grating-like structurized object 15 to be measured, which order is known to be not affected by the grating structure of the diffracting object 15, impinges on an observation screen 6. A component 29 passing through beam splitter 5 also impinges on grating-like structurized object 15 to be checked and is diffracted there in a known manner. The first diffraction order 33 of this radiation, which is represented by dashed lines and which is known to be affected by the characteristics of the grating-like structurized object 15 interferes with component 32 which is not affected by the object to be measured and generates an interference fringe field on observation screen 6. The arrangement is such that with a given grating constant and with a uniform grating structure of object 15 to be checked both components 32 and 33 are parallel to each other and generate on observation screen 6 a uniform interference fringe pattern having specific distances. The statements made in connection with FIG. 1 regarding the forming of the pattern shown in FIG. 5 also apply to FIG. 3. In case of local disturbances of the uniform grating structure of object 15 to be measured the first order diffracted in these areas will have a different direction, which leads to disturbances as shown for instance in FIG. 6, of the interference fringe field visible on observation screen 6. A change of the grating constant or of the angular position of object 15 to be measured will also result in changes of the interference fringe field generated on observation screen 6.

Figure 4:
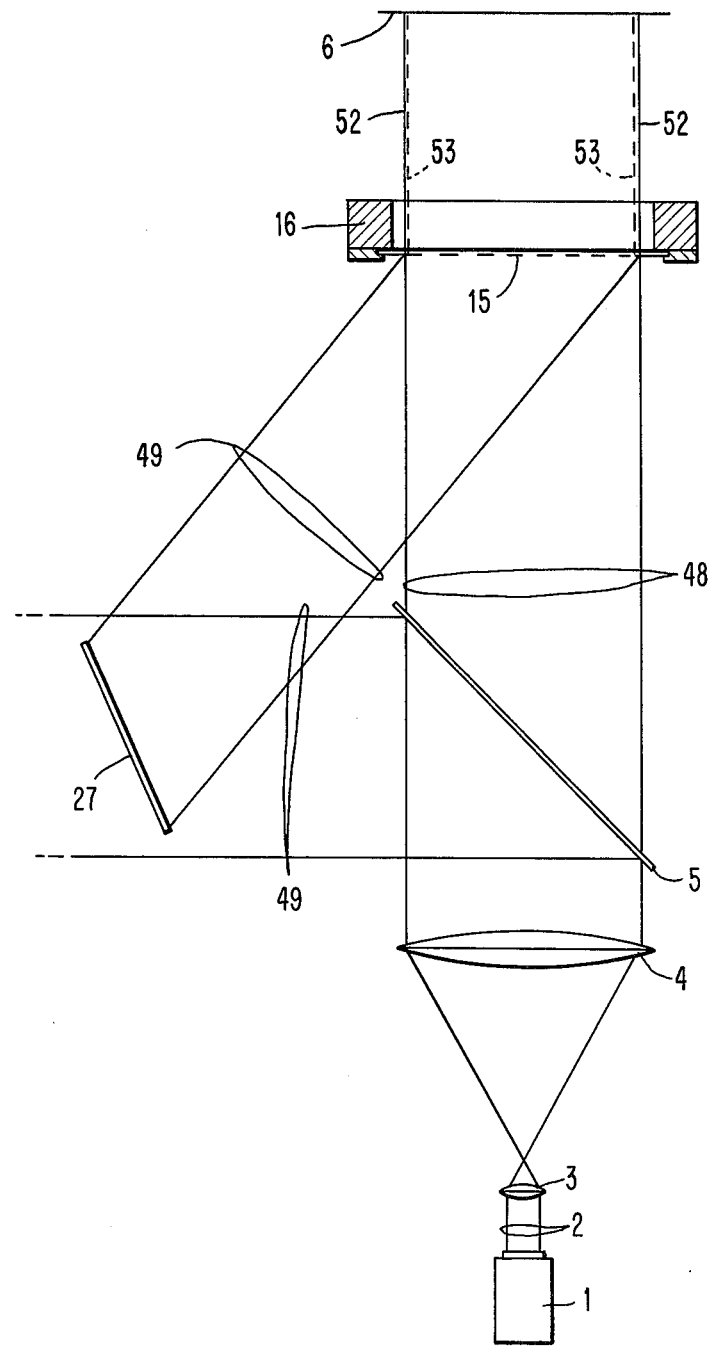

Refer now to FIG. 4 which illustrates an embodiment for checking an object 15 to be measured which shows the characteristics of a transmission grating. A monochromatic and coherent light beam 2 emanating from a light source 1 designed for instance as a laser is expanded by lenses 3 and 4 and directed to a beam splitter 5. A component 49 reflected at this beam splitter is reflected at a mirror 27 and impinges, at an angle different from 0°, onto an object 15 to be measured which shows the characteristics of a transmission grating. A component 48 passing beam splitter 5 impinges vertically on object 15 to be measured and is diffracted there in a known manner under different orders. The zero'th diffraction order 52 represented by solid lines, of this component which is known to be not affected by the characteristics of the grating-like structurized object 15 to be measured impinges vertically onto an observation screen 6. Component 49, impinging on object 15 to be measured at an angle differing from 0°, is also diffracted in a manner known per se under different orders at object 15 to be measured. The first order 53 represented by dashed lines which is known to be affected by the characteristics of grating-like structurized object 15 to be measured interferes with component 52 and generates an interference fringe pattern at observation screen 6. The arrangement is such that with a predetermined and uniform grating constant of the grating-like structurized object 15 to be measured the two components 52 and 53 are parallel to each other and form, at observation screen 6, a uniform interference fringe field having uniform distances. In case of local disturbances of the uniform grating structure of object 15 to be measured the first order 53 diffracted in the respective areas no longer extends in parallel to component 52 so that disturbances are visible in the corresponding areas of observation screen 6. The same applies also, as described in connection with the specification of the preceding figures, to deviations of the angle position of object 15 around an axis that is parallel to the drawing plane, and for changes of the grating constant of the structure of object 15 to be measured.

In the apparatus shown in FIGS. 1 to 4 objects 15 to be tested are held by suitable carrier elements 16.

It is evident that in the above described apparatus only changes of the grating structure in the direction of the grating plane are visible on observation screen 6, whereas irregularities of the planarity of the grating-like structurized object 15 to be tested in no way affect the interference fringe fields.

With continued reference to FIGS. 1 to 4, refer again particularly to FIG. 3, for a further description of the present invention. In FIG. 3, object 15, having a grating-like structure, is radiated with two plane wavefronts 28 and 29. These wavefronts 28 and 29 are linearly polarized in the same direction, and are applied from two different directions forming an angle $\theta$.

In the case where the grating-like structurized object 15 shows the characteristics of an ideal grating with the grating constant:

$$g = g_0 = \lambda / \sin \theta \quad (1)$$

the radiation consisting of wavefront 28 extends as its zero'th order 32 diffracted at object 15, in parallel to the first order 33 of radiation 29 diffracted at the same object.

If $g \neq g_0$, radiation components 32 and 33 no longer extend in parallel to each other but in two different direction. Owing to the combination of these components an interference fringe field consisting of bright and dark fringes is formed on an observation screen 6, as shown for instance in FIG. 5 for a grating structure with uniform grating constant, and in FIG. 6 for a grating structure that is disturbed locally for instance due to local heat influence.

For an object 15 disposed in parallel to an observation screen 6, as illustrated in FIGS. 1, 2 and 4, the distance between adjacent fringes is obtained by the following formula:

$$\Delta = \frac{g}{1 - \frac{g}{\lambda} \sin \theta} = \frac{g}{1 - \frac{g}{g_0}} \quad (2)$$

From formula (2) it is concluded that with an increasing difference $g - g_0$ the fringe distance $\Delta$ is decreasing. For a visual detection of the deviation, $\Delta$ must not be greater than the planar expansion of the object grating. On the other hand, the fringe density must not exceed the resolution limit of the eye. The change of length of an object of 100 mm by 1 μm for example is easily detected.

There applies:

$$\frac{g}{g_0} = \frac{100 + 10^{-3}}{100} = 1 + 10^{-5}$$

$$\Delta = \frac{g}{10^{-5}}$$

For $\Delta = 100$ mm there follows
$g = 10^{-3} = 1$ μm

A smaller fringe spacing and thus an increase of resolution can be achieved with a grating of the grating constant $g < 1$ μm. Gratings up to $g = 0.3$ μm are commercially available.

A further increase of the measuring sensitivity is possible also without a further decrease of the grating constants of the test object, for if the angle $\theta = \theta^*$ between two illuminated light beams is selected in such a manner that:

$$\sin \theta^* = \frac{2\lambda}{g}, \frac{3\lambda}{g}, \ldots \quad (3)$$

by superposition with the respective +2nd, +3rd, ... diffraction orders of the grating it is possible to reach a duplication, triplication, etc., of the resolution. This corresponds to the increase of the resolution, at a decrease of the grating constant of the object grating to:

$$g^* = \frac{g}{2}, \frac{g}{3} \ldots \quad (4)$$

In the formula relations derived above and in the following, the grating constant g is to be replaced by g*.

The above discussion is restricted to a uniform expansion or shrinking, respectively, of the entire object surface. The field of observation is covered with a uniform line raster.

Local structural changes in the object surface can be detected, too. They result in a distortion of the line pattern that can be observed. This means that overlay deviations from a standard can be detected and quantitatively determined by the process.

By turning the object grating by an angle $\psi$, the field of observation is covered with a line raster. The line spacing is:

$$\Delta = \frac{g_o \cdot g}{\sqrt{g^2 + g_o^2 - 2gg_o \cdot \cos\psi}} \quad (5)$$

1. In the specific case of $\psi = 0$ there is $$\Delta = \frac{g_o \cdot g}{\sqrt{(g-g_o)^2}} = \frac{g_o \cdot g}{g - g_o} = \frac{g}{1 - \frac{g}{g_o}} \quad (6)$$

which is relation (2).

2. In the case of $g = g_o$ $\psi \neq 0$ there applies:

$$\Delta' = \frac{g^2}{\sqrt{2g^2 - 2g^2 \cos\psi}} = \frac{g}{2\sin\frac{\psi}{2}}$$

A linear deviation of grating constant g from $g_o$ cannot be detected when the grating is angularly rotated. It is only visible at $\psi=0$. On the other hand, the rotation permits the proof of local deviations of the grating constants over the entire object to be measured.

By means of angularly rotating the grating, a fine division of the entire range to be measured (object surface) can be reached up to $$\Delta' = \frac{g}{\sqrt{2}}.$$

If the division exceeds the resolution possible for the human eye a structural distortion can be made visible for a fixed $\Delta'$ in that in the observation plane a reference grating with the grating constant $\Delta'$ is arranged. Thus, a new visible line system (Moire pattern) is achieved which provides information about micro-distortions in the measuring zone.

Thus, the interference fringe field of FIG. 5 was produced by illumination of an error-free grating, where the grating lines enclose with the plane of incidence an angle $\delta$ which was neglibibly smaller than 90°. In the above formulas the angle $\psi = 90° - \delta$ was employed for better understanding.

While the invention has been particularly shown and described with reference to preferred embodiments thereof, it will be understood by those skilled in the art that various changes in form and detail may be made therein without departing from the spirit and scope of the invention.

What is claimed is:

1. Interferometric apparatus for determining and measuring defects on an object comprising:
    a coherent light source;
    a beam expanding means for expanding the beam provided by said coherent light source;
    a beam splitting means positioned in the beam path for splitting said beam into first and second components;
    a stationary object having a periodically structured surface positioned in a plane at a fixed angle with respect to said beam splitting means;
    a first mirror for reflecting one of said first and second components onto said object, causing the said one of said first and second components to be diffracted from said object;
    said beam splitting means being positioned in the path of said diffracted beam such that said first and second components thereby interfere with each other; and
    display means for observing resultant interference patterns formed by said first and second components.

2. Apparatus as in claim 1 wherein said display means is placed in a plane parallel to the object.

3. Apparatus as in claim 1 further comprising: a second mirror in the beam path between said beam splitting means and said first mirror for reflecting one of said first and second components.

4. Apparatus as in claim 1 wherein said display means is placed in a plane that is angularly disposed with respect to the object.

5. Apparatus as in claim 1 wherein said beam splitting means is physically between said object and said display means.

6. An interferometric process for determining and measuring defects, and for the positioning of objects having periodically structurized surfaces, by means of interference of beams modulated and not modulated at the object to be checked, comprising the steps of:

7. A process as in claim 6 wherein:
    said second component is reflected into a beam path of an order differing from 0 of the radiation diffracted at the object.

8. A method as in claim 6 wherein:
    said first and second components are linearly polarized in the same direction with respect to each other.

* * * * *